United States Patent
Ozaki et al.

(10) Patent No.: US 7,762,956 B2
(45) Date of Patent: Jul. 27, 2010

(54) ELECTRONIC BLOOD PRESSURE METER

(75) Inventors: Shinobu Ozaki, Kitamoto (JP);
Shigenobu Toda, Kitamoto (JP);
Toshiharu Aiba, Kitamoto (JP)

(73) Assignee: A & D Company, Ltd., Tokyo (JP)

( * ) Notice: Subject to any disclaimer, the term of this patent is extended or adjusted under 35 U.S.C. 154(b) by 643 days.

(21) Appl. No.: 10/576,851

(22) PCT Filed: Jul. 28, 2004

(86) PCT No.: PCT/JP2004/010730

§ 371 (c)(1),
(2), (4) Date: Jul. 12, 2006

(87) PCT Pub. No.: WO2005/039408

PCT Pub. Date: May 6, 2005

(65) Prior Publication Data

US 2007/0066903 A1    Mar. 22, 2007

(30) Foreign Application Priority Data

Oct. 28, 2003   (JP) ............................. 2003-366795

(51) Int. Cl.
*A61B 5/02*   (2006.01)
(52) U.S. Cl. ................... 600/485; 600/490; 600/495; 600/500
(58) Field of Classification Search ............ 600/481, 600/490, 500, 495
See application file for complete search history.

(56) References Cited

U.S. PATENT DOCUMENTS

| | | | | |
|---|---|---|---|---|
| 3,654,915 A | * | 4/1972 | Sanctuary | 600/495 |
| 4,397,317 A | * | 8/1983 | Villa-Real | 600/493 |
| 4,944,304 A | * | 7/1990 | Nishina | 600/480 |
| 5,649,536 A | * | 7/1997 | Ogura et al. | 600/493 |
| 6,726,632 B2 | * | 4/2004 | Tampo et al. | 600/481 |
| 2002/0072860 A1 | | 6/2002 | Amano | |
| 2002/0120199 A1 | * | 8/2002 | Ogura et al. | 600/485 |
| 2003/0060721 A1 | * | 3/2003 | Nakazawa et al. | 600/490 |
| 2003/0069751 A1 | * | 4/2003 | Lichtenstein et al. | 705/2 |

(Continued)

FOREIGN PATENT DOCUMENTS

EP    1086650    3/2001

(Continued)

*Primary Examiner*—Robert L Nasser
*Assistant Examiner*—Michael D'Angelo
(74) *Attorney, Agent, or Firm*—Jordan and Hamburg LLP (57) ABSTRACT

There is provided an electronic sphygmomanometer that permits a user to visually recognize easily that he or she started measurement by manipulating his or her identification key and that his or her measured value is being displayed on a display unit. The electronic sphygmomanometer 10 includes blood pressure measuring means 26 for measuring a blood pressure value, a display unit 28 for displaying the blood pressure value, a plurality of user identification keys 34 selectable by respective users, and a plurality of light emitting means 36 disposed corresponding to the respective user identification keys 34. When a user identification key A34a is manipulated, a measured blood pressure value is stored in the memory corresponding to the manipulated user identification key 34a, and the light emitting means A'36a corresponding to the manipulated user identification key A34a emits light while the blood pressure value of the user is being measured and/or being displayed.

12 Claims, 5 Drawing Sheets

U.S. PATENT DOCUMENTS

2003/0135087 A1 * 7/2003 Hickle et al. .................. 600/26
2003/0158487 A1 * 8/2003 Thede et al. ................. 600/485

FOREIGN PATENT DOCUMENTS

| JP | 5-137697 | 6/1993 |
| JP | 5-30724 | 8/1993 |
| JP | 2002-272686 | 9/2002 |

* cited by examiner

ELECTRONIC BLOOD PRESSURE METER

TECHNICAL FIELD

The present invention relates to an electronic blood pressure meter (hereinafter, "electronic sphygmomanometer") for automatically measuring and displaying a blood pressure value, and more particularly to an electronic sphygmomanometer shared by a plurality of users or in a plurality of events.

BACKGROUND ART

Recently, electronic sphygmomanometers become widespread in place of mercury sphygmomanometers and aneroid sphygmomanometers. Various types of electronic sphygmomanometers such as a small/single function type sphygmomanometer, a multi-function type sphygmomanometer with a memory, a printer and the like, etc. are made available on the market to accommodate applications of users.

In step with this tendency, a practice of measuring a blood pressure value using an electronic sphygmomanometer is established at home as a means of health management.

Under such circumstances, there is developed a sphygmomanometer such as the sphygmomanometer disclosed in a patent document 1 which can securely store, when it is shared by a plurality of users, measured values of the respective users using a changeover switch.

However, the sphygmomanometer has technical problems as described below.

Parent Document 1: Japanese Patent Laid-open Publication No. 2002-272686

PROBLEMS THAT THIS INVENTION IS TO BE SOLVED

The sphygmomanometer disclosed in the patent document 1 employs such a construction that an identification symbol of a user is displayed on a display unit together with a measured value. However, if the user does not grasp his or her identification symbol, it is meaningless to display the identification symbol. Further, since a display space is limited, the above arrangement is defective to an elderly person in that it is difficult for him or her to recognize a displayed identification symbol because it is small in size.

Further, in the sphygmomanometer disclosed in the patent document 1, although the user is switched by movement of a changeover switch, a switching job is troublesome to the user, and there may be such a case that the user starts measuring a blood pressure value while forgetting the switching job or his or her measured value is stored in the memory of other user.

An object of the present invention, which was made in view of the conventional problems, is to provide an electronic sphygmomanometer by which a user can visually and easily recognize that measurement is started when the user manipulates his or her identification key and that his or her measured value is displayed on a display unit and which can store measured values of respective users and respective events without using a switching means.

To achieve the above object, the electronic sphygmomanometer according to the present invention includes a blood pressure measuring means for measuring a blood pressure value, a display unit for displaying the blood pressure value, a plurality of user identification keys selectable by respective users, and a plurality of light emitting means each disposed in correspondence to each of the user identification keys, wherein a measured blood pressure value is stored in a memory corresponding to the manipulated user identification key by manipulating the user identification key, and the light emitting means corresponding to the manipulated user identification key emits light while the blood pressure value of the user is being measured and/or being displayed.

According to the electronic sphygmomanometer arranged as described above, since the light emitting means corresponding to the manipulated user identification key emits light while the blood pressure value is being measured and displayed, the user can visually recognize that measurement is executed by manipulating his or her identification key, that his or her blood pressure value is being displayed, a process of measurement, and the like at a glance.

Further, the blood pressure measuring means can start measuring a blood pressure value in association with the manipulation of the user identification key.

According to the arrangement, since the measurement of the blood pressure value is started in association with the manipulation of the user identification key, the user does not forget to execute a switching job for switching a user changeover switch, and a measured value is securely stored in a memory prepared for each user.

Further, the display unit can display a previously stored value stored in the memory corresponding to the manipulated user identification key in association with the manipulation of the user identification key.

According to the arrangement, since the previously measured value of the user himself or herself, which is not the previously measured value of any other user, is securely displayed, it is possible to use the displayed value for health management and the like.

The electronic sphygmomanometer includes a power supply unit for supplying operation power to electric/electronic circuits in a main body thereof, and the power supply unit can supply the power to the inside of the main body in association with the manipulation of the user identification key.

According to the arrangement, it is possible to start measuring a blood pressure value and to display it at once without manipulating a power supply key.

Further, the light emitting means can emit light of different color for each of the user identification keys corresponding to the light emitting means.

According to the arrangement, the user can visually recognize that he or she manipulates his or her key and that his or her blood pressure value is being displayed also by color, in addition to the locations where the user identification keys are disposed, and symbols.

Further, an electronic sphygmomanometer includes blood pressure value measuring means for measuring a blood pressure value, a display unit for displaying the blood pressure value, a plurality of event identification keys selectable by respective events, and a plurality of light emitting means disposed in correspondence to the event identification keys, wherein a measured blood pressure value is stored in the memory corresponding to a manipulated event identification key by manipulating the event identification key, and the light emitting means corresponding to the manipulated event identification key emits light while the blood pressure value is being measured and/or being displayed.

According to the electronic sphygmomanometer arranged as described above, since the light emitting means corresponding to the manipulated event identification key emits light while a blood pressure value is being measured and displayed, the user can visually recognize that measurement is being executed by manipulating an arbitrary event, that his or her blood pressure value is being displayed, a process of measurement, and the like at a glance.

Further, the blood pressure measuring means can start measuring a blood pressure value in association with the manipulation of the event identification key.

According to the arrangement, since measurement of a blood pressure value is started in association with manipulation of the event identification key, the user does not forget to execute a switching job for switching a user changeover switch, and a measured value is securely stored in a memory prepared for each event.

Further, the display unit can display the previously stored value stored in the memory corresponding to the manipulated event identification key in association with the manipulation of the event identification key.

According to the arrangement, since the previously measured value in the same type of event, which is not the previously measured value in any other type of event, is securely displayed in association with the manipulation of the event identification key, the displayed value can be used for the health management and the like.

Further, the electronic sphygmomanometer includes a power supply unit for supplying operation power to electric/electronic circuits in a main body thereof, and the power supply unit can supply the power to the inside of the main body in association with the manipulation of the event identification key.

According to the arrangement, it is possible to start measuring a blood pressure value and to display it at once without manipulating the power supply key.

Further, the light emitting means can emit light of different color to each of the event identification keys corresponding to the light emitting means.

According to the arrangement, the user can visually recognize that a key corresponding to an event is manipulated and that a blood pressure value in the event is being displayed also by color, in addition to the locations where the event identification keys are disposed, and symbols.

Further, the memory may store supplemental information such as a blood pressure value measuring time and the like in association with the blood pressure value, in addition to the blood pressure.

As described above, storing the supplemental information in the memory in addition to the blood pressure value is helpful to observe, diagnose, and analyze the state of health of the user.

Further, the electronic sphygmomanometer includes a time measuring means, and the light emitting means, which corresponds to the event identification key corresponding to a present time clocked by the time measuring means, may emit light based on the present time.

According to the arrangement, the user can grasp which event identification key is to be manipulated to measure a blood pressure value at a glance.

EFFECT OF THE INVENTION

According to the electronic sphygmomanometer of the present invention, the light emitting means corresponding to the manipulated user identification key or the manipulated event identification key is lit or flashed while the blood pressure value is being measured or displayed. Therefore, the user can visually recognize at a glance that he or she has executed measurement by manipulating his or her identification key, that his or her blood pressure value is being displayed, a process of measurement, and that he or she executes measurement and display by selecting an arbitrary event.

Further, since measurement of a blood pressure value is started in association with the manipulation of the event identification keys, the user does not forget to execute a switching job for switching a user changeover switch, and a measured value is securely stored in a memory prepared for each user or each event.

Further, since the previously measured value of the user himself or herself, which is not the previously measured value of any other user, and the previously measured value in the same type of event, which is not the previously measured value in a different type of event, are securely displayed, the displayed values can be used for health management and the like.

BEST MODE FOR CARRYING OUT THE INVENTION

Figure 1:
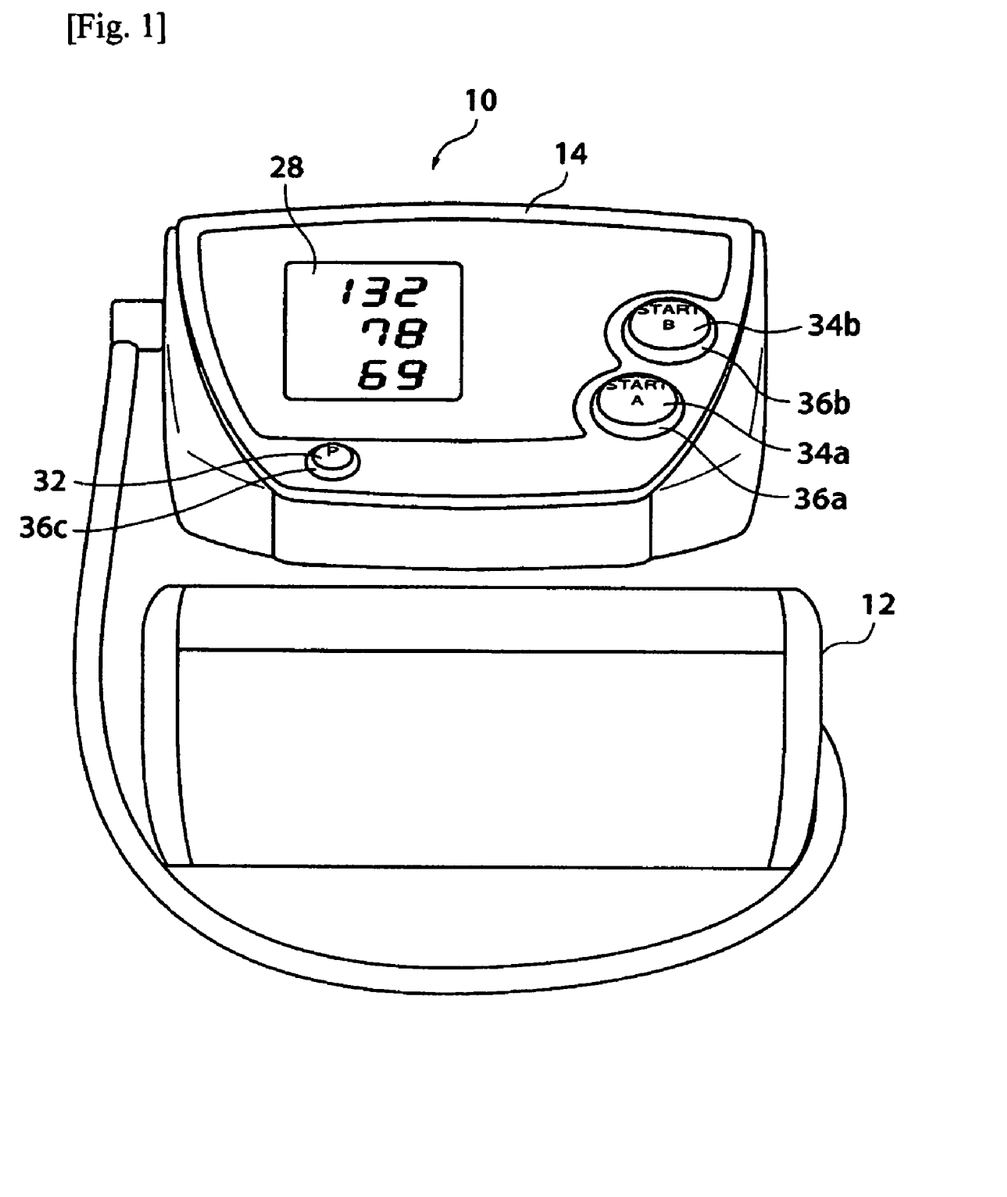
FIG. 1 is an outside appearance view showing an example of an electronic sphygmomanometer according to the present invention.
Figure 2:
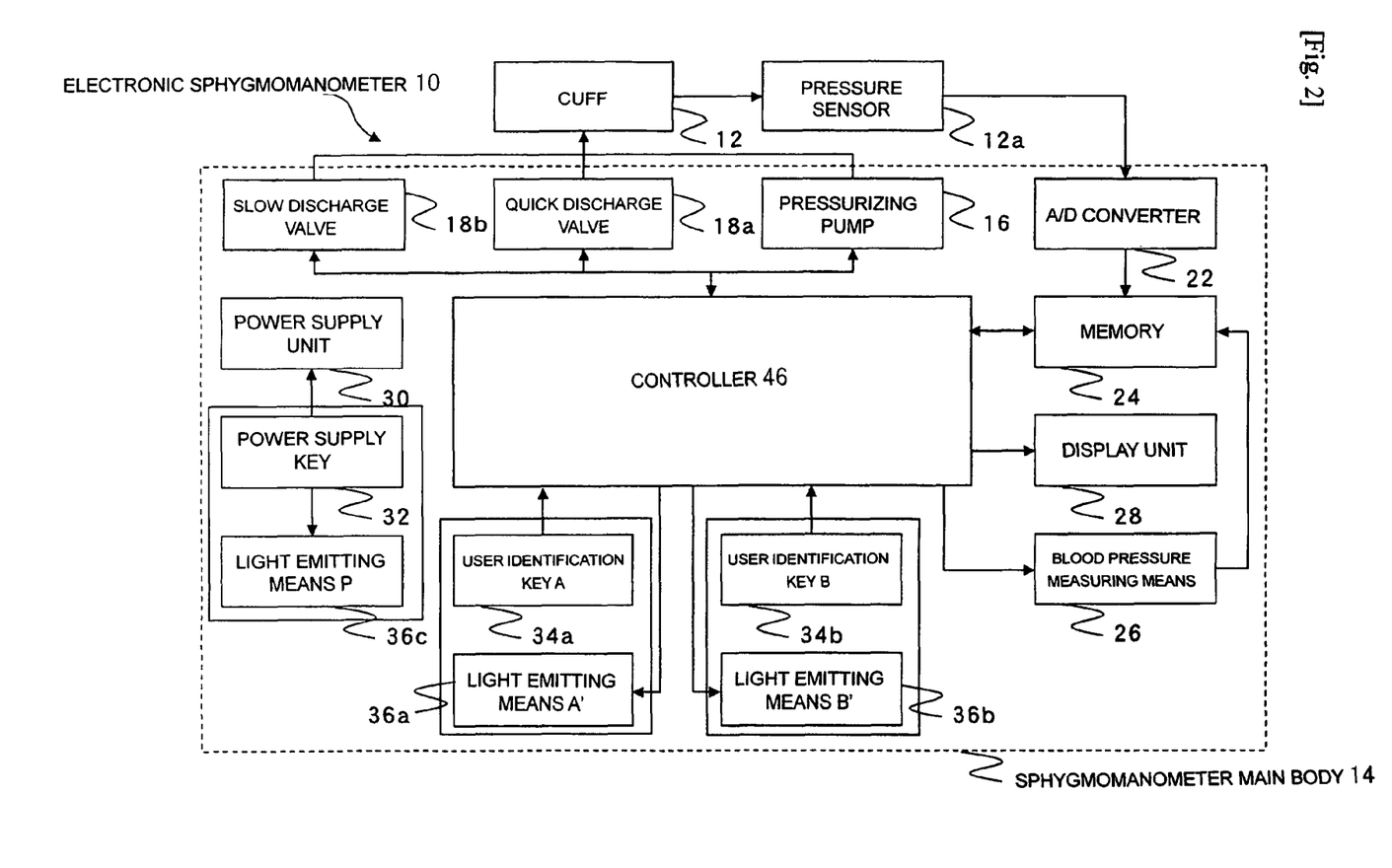
FIG. 2 is a configurational view showing the example of the electronic sphygmomanometer according to the present invention.

A preferable embodiment of the present invention will be described below in detail based on accompanying drawings. FIG. 1 is an outside appearance view showing an example of an electronic sphygmomanometer 10, and FIG. 2 is a configurational view showing the example of the electronic sphygmomanometer 10.

The electronic sphygmomanometer 10 shown in these figures includes a cuff 12 and a sphygmomanometer main body 14. The cuff 12 is worn around a portion, to which pressure can be applied, of the artery of a living body and includes a pressure sensor 12a for detecting the pressure in the artery.

Although the electronic sphygmomanometer 10 of the example is an electronic sphygmomanometer of a type whose cuff 12 is worn around an upper arm, since the cuff 12 of the present invention may be worn around any portion, the electronic sphygmomanometer 10 of the present invention may be realized by a type whose cuff 12 is worn around a wrist or a finger.

The sphygmomanometer main body 14 has a pressurizing pump 16, a quick discharge valve 18a, and a slow discharge valve 18b disposed therein and they communicate with and are connected to the inside of the cuff 12.

The pressurizing pump 16 constitutes a pressurizing means for supplying pressurized air into the cuff 12. On the completion of measurement of a blood pressure value, and the like, the quick discharge valve 18a quickly discharges the pressurized air filling the inside of the cuff 12.

The slow discharge valve 18b constitutes pressure reducing means for gradually reducing the pressure in the cuff 12 in a state that the pressurizing operation of the pressurizing pump 16 is interrupted after the inside of the cuff 12 reaches predetermined pressure by being supplied with pressurized air.

Note that the electronic sphygmomanometer 10 of the example is a type of an electronic sphygmomanometer that employs a system of calculating a blood pressure value in a pressure reducing process of the cuff 12, it may be a type for calculating the blood pressure value in a pressure increasing process of the cuff 12. In this case, the slow discharge valve 18b is not necessary.

The above-mentioned control including the actuation, interruption, and the like of the pressurizing pump 16, the quick discharge valve 18a and the slow discharge valve 18b is executed in response to a control signal output from a controller 20 disposed in the sphygmomanometer main body 14 based on a value detected by the pressure sensor 12a disposed in the cuff 12 and on the amount of pressurization to the pressurizing pump 16 that is stored in a memory 24 connected to the controller 20.

Note that the value detected by the pressure sensor 12a is input to the controller 20 through an A/D converter 22. The A/D converter 22 may be built in the controller 20, and, in this case, the value detected by the pressure sensor 12a is directly input to the controller 20.

A blood pressure measuring means 26 is means for calculating a blood pressure value based on a pulse wave signal of the artery of the living body, that is, based on the value detected by the pressure sensor 12a. In the example, the detected value of the pressure sensor 12a, which is input to the controller 20 in the pressure reducing process of the cuff 12, is stored in the memory 24 and used to measure a blood pressure value.

In a blood pressure measuring method called an oscilometric method, the pressure value in the cuff 12 at the point where the amplitude of the pulse wave signal abruptly increases in the pressure reducing or increasing process of the cuff 12 is used as a maximum blood pressure value, the pressure value in the cuff 12 at the point where the amplitude of the pulse wave signal abruptly decreases is used as a minimum blood pressure value, and the blood pressure value in the cuff 12 at the point where the amplitude of the pulse wave signal is maximized is used as an average blood pressure value.

Accordingly, the blood pressure measuring means 26 calculates the maximum blood pressure value and the minimum blood pressure value by differentiating the detected value of the pressure sensor 12a and comparing a degree of increase/decrease with a prescribed value and calculates the average blood pressure value by comparing the magnitudes of respective amplitudes and includes an arithmetic operation unit necessary to calculate them.

The controller 20 displays a measured blood pressure value on a display unit 28 to be described later and stores it in the memory 24 to display a history and to execute analysis and the like of the time-series change of a blood pressure value, in addition to that it instructs the blood pressure measuring means 26 to start measurement.

Note that respective manufacturers employ various blood pressure value determination methods and determination standards, and the electronic sphygmomanometer 10 according to the present invention need not always measure a blood pressure value by the oscilometric method. Further, whether the arithmetic operation unit for constituting the blood pressure measuring means 26 is realized by a circuit using electronic parts or by a program of a CPU is variously determined depending on applications and the like, and a constitutional means included in the blood pressure measuring means 26 may be included in the controller 20.

Further, the display unit 28 is disposed on the front surface side of the sphygmomanometer main body 14 to display the blood pressure value measured by the blood pressure measuring means 26, the blood pressure value stored in the memory 24, and the like. Note that the display unit 28 can also display the information of the average blood pressure value, a pulse rate, and the like, in addition to the maximum blood pressure value and the minimum blood pressure value.

A power supply unit 30 is built in the sphygmomanometer main body 14 to supply operation power to the electric/electronic circuits of the controller 20, the blood pressure measuring means 26, the pressurizing pump 16, the quick discharge valve 18a, the slow discharge valve 18b, the display unit 28, and the like in the sphygmomanometer main body 14. The power supply unit 30 is generally composed of a direct current power supply such as a battery and the like in consideration of convenience when the electronic sphygmomanometer 10 is carried. However, the power supply unit 30 may be composed of an alternate power supply, and when the electric/electronic circuits in the sphygmomanometer main body 14 is operated by a direct current power supply, an alternate current/direct current converter may be built in.

Further, a power supply key 32 for activating the power supply unit 30, a plurality of user identification keys 34, which can be selected by respective users, and a plurality of light emitting means 36, which are disposed in correspondence to the respective keys, are connected to the controller 20 and disposed on the front surface of the sphygmomanometer main body 14.

Although the power supply key 32 is generally composed of a push button, it does not matter whether it employs a lock type or a non-lock type, and the power supply key 32 may be composed of a slide switch for discriminating whether power is turned on or off. Further, the location in which the power supply key 32 is disposed may be a side surface of the sphygmomanometer main body 14 in place of the upper surface thereof shown in FIG. 1.

Although the user identification keys 34 is generally composed of a circular non-lock push button switch as shown in FIG. 1, it may be composed of other switch as along as it can output a signal showing that a key is manipulated, may be formed in any shape, and may or may not be provided with a lock.

The light emitting means 36 are disposed just below or in the peripheries of the user identification keys 34, are composed of LEDs (light emitting diodes) and the like, emit light based on a control signal from the controller 20 or a key manipulation detecting signal, and illuminate the keys and the peripheries thereof. The light emitting means 36 may emit light of different color for each of the user identification keys 34. When the light emitting means 36 are disposed just under the keys, the keys are generally composed of a transparent or semi-transparent resin so that light is irradiated to the keys themselves. Further, when the peripheries of the keys are illuminated with light, a ring-shaped transparent or semi-transparent resin is fitted to cover the outer periphery of each circular key so that light leaks from the resin portion as shown in, for example, FIG. 1.

It should be noted that the periphery of the key means an arbitrary region within a range where it is apparent that the light emitting means 36 corresponds to the key such as just on, just under, and the like of the surface on which the key is disposed and does not mean to surround the entire periphery of the key. Further, the light emitting means 36 may be formed in a circular shape, a square shape or the shape of the LED itself, in addition to the above ring shape.

A feature of the electronic sphygmomanometer 10 according to the present invention resides in that the blood pressure value measured by the blood pressure measuring means 26 is stored in the memory region of the memory 24 corresponding to the user identification key 34 being manipulated in response to the manipulation of the user identification key 34. Further, the feature resides in that the light emitting means 36 corresponding to the manipulated user identification key 34 emits light while a blood pressure value is being measured by the blood pressure measuring means 26 and while the blood pressure value is being displayed on the display unit 28.

Memory regions as many as the user identification keys 34 are formed in the memory 24 so as to correspond to the user identification keys 34. The controller 20 detects that the user manipulates an arbitrary user identification key 34 that is previously determined and selected by him or her and stores a measured blood pressure value in the memory region corresponding to the manipulated user identification keys 34. That is, the blood pressure value of each user is stored in the memory 24.

Then, the controller 20 controls the light emission of the light emitting means 36 corresponding to the manipulated user identification key 34 from the start to the end of measurement of a blood pressure value and/or while the blood pressure value is being displayed, and whereby the user can visually confirm that the blood pressure value is being measured and displayed securely even while the blood pressure value is being measured and displayed by manipulating his or her user identification keys 34.

Since the light emitting means 36 are disposed just under or in the peripheries of the user identification keys 34 and the user identification keys 34 themselves or the peripheries thereof are lit or flashed, they can be more easily observed than the case that user identification symbols and symbols for indicating that measurement is being executed are displayed in the display unit 28. As a result, even old persons and children can visually confirm them easily.

When the light emitting means 36 emit light not only while the blood pressure value is being measured but also when the measured blood pressure value is displayed on the display unit 28 after the completion of measurement thereof, a method of controlling the light emission may be changed such that, for example, light is flashed during measurement and lit during display. With this operation, the user can visually confirm not only that his or her user identification key 34 is manipulated but also that the process of measurement (start and end of measurement, and display).

Further, spaces, on which seals are adhered or characters are directly written, may be formed in the vicinities of the user identification keys 34 so that users do not forget the previously determined user identification keys. With this arrangement, the users do not get flustered when they manipulate identification keys 34.

The blood pressure measuring means 26 may start measuring a blood pressure value in association with manipulation of any user identification key 34. If a plurality of the users are identified by manipulating a changeover switch for switching the users in place of manipulating the user identification keys 34, the users may start measuring a blood pressure value while forgetting to switch the changeover switch.

In the above arrangement, however, the measurement of the blood pressure value is not started without fail unless the user identification key 34 is manipulated. Accordingly, the measurement of the blood pressure value is not started while forgetting to manipulate the changeover switch, and the blood pressure value of the user can be securely stored in his or her memory region.

Further, since it is not necessary to manipulate a measurement start key and the like, the controller 20 can start measuring the pressure value at once when the user manipulates the user identification key 34 after the power supply key 32 is manipulated.

Note that after the power supply key 32 is manipulated, all the light emitting means 36 corresponding to all of the user identification keys 34 may emit light based on a control signal from the controller 20. With this operation, after the sphygmomanometer main body 14 is energized, it is possible to prompt the user to manipulate any of the user identification keys 34.

The user identification keys 34 and the measurement start key (not shown) may be disposed independently, respectively. In this case, to prevent the user from forgetting to manipulate the user identification key 34, the controller 20 must execute such a control that measurement of a blood pressure value cannot be started unless it is detected that both the measurement start key and any of the user identification keys 34 are manipulated. It is sufficient to provide at least one set of the measurement start key.

Further, the display unit 28 may display the value previously stored in the memory region of the memory 24 corresponding to the manipulated user identification key 34, that is, the previously measured value stored in the memory region of the user when a blood pressure value was measured last time in association with the manipulation of the user identification key 34.

Since the previously measured value of the user who manipulates the user identification key 34 is securely stored in the memory region corresponding to the manipulated user identification key 34, the blood pressure value of other user is prevented from being displayed, whereby the previously measured value can be referred to for health management. Further, when the previously measured value of the user is displayed, since it is called from the memory 24 and displayed on the display unit 28 at once by the manipulation of the user identification key 34 without the need of executing the switching job by the changeover switch and the like, it is not necessary to provide a display key and the like.

Further, since the light emitting means 36 corresponding to the manipulated user identification key 34 emits light as described above also when the display unit 28 displays the previously measured value, the user can visually recognize easily that his or her previously measured value is displayed by manipulating his or her user identification key 34.

Note that a previously measured value display key may be provided independently of the user identification keys 34, and the previously measured value of the user who manipulates the previously measured value display key and any of the user identification keys 34 may be displayed on the display unit 28 (order for manipulating the keys is not matter). It is sufficient to provide at least one set of the previously measured value display key also in this case likewise the measurement start key described above.

When neither the measurement start key nor the display key is provided to start measurement of a blood pressure value and to display the previously measured value together in association with the manipulation of the user identification key 34, a manipulation procedure and a manipulation time are changed to discriminate both the functions such that the previously measured value is displayed when the user identification key 34 is depressed for a long time (for example, about 2 seconds) and the measurement of the blood pressure value is started when it is depressed for a short time.

Further, the power supply unit 30 may supply power to the inside of the sphygmomanometer main body 14 in association with the manipulation of the user identification key 34. With this manipulation, the power supply key 32 becomes unnecessary, and energization of the sphygmomanometer main body 14, measurement of the blood pressure value, storage of the measured blood pressure value in the memory, and the display thereof can be sequentially executed by only manipulating any of the user identification keys 34, whereby the manipulation executed on the user side can be simplified.

When the user identification key 34 is also used as the measurement start key and the previously measured value display key, it is preferable to change the manipulation procedure and the manipulation time of the key such that when the user identification key 34 is depressed for a short time, power is supplied as well as measurement of a blood pressure value is stated, and when it is depressed for a long time, power is supplied as well as a previously measured value is displayed.

EXAMPLE 1

Figure 3:
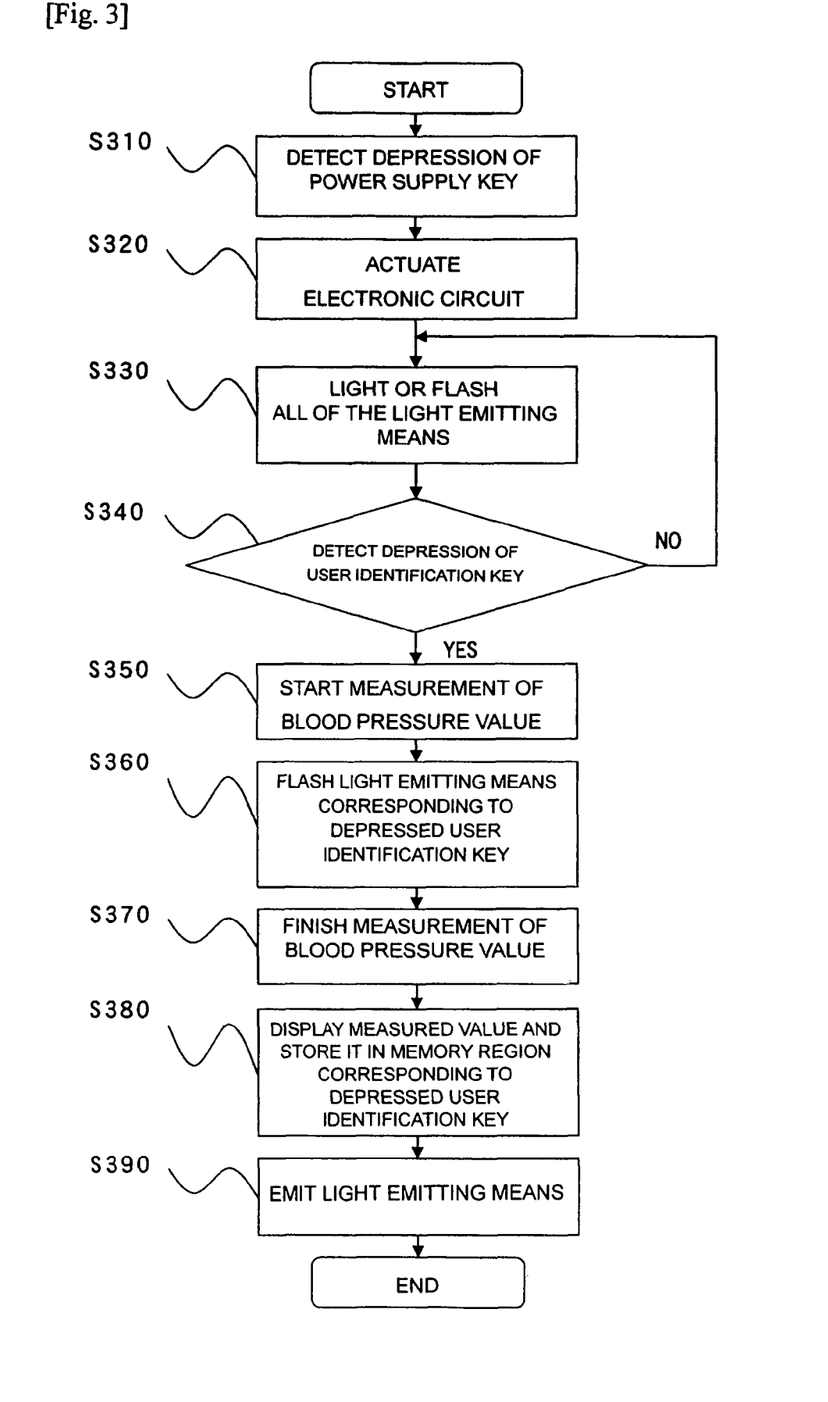
FIG. 3 is a flowchart showing a first example of the electronic sphygmomanometer according to the present invention.

The overall operation of an electronic sphygmomanometer 10 of an example 1 will be explained below with reference to a flowchart of FIG. 3. As the premise of the flowchart, it is assumed that a user wears a cuff 12 around an upper arm to measure a blood pressure value. Further, of user identification keys A34a and B34b included in the electronic sphygmomanometer 10, the user determines that the user identification key A34a is his or her identification key. Note that although the two user identification keys 34 are provided in the example as shown in FIG. 1, the number of the user identification keys 34 is not limited to the member of examples described herein.

A sphygmomanometer main body 14 detects that a power supply key 32 is depressed and transmits it to a power supply unit 30 (S310). The power supply unit 30 generates power necessary to all the electric/electronic circuits such as a controller 20 and the like in the sphygmomanometer main body 14 and supplies it to respective components (S320). At the time, since the power is also supplied to a light emitting means P36c corresponding to the power supply key 32, the light emitting means P36c emits light, and the user can visually recognize that the sphygmomanometer main body 14 is energized.

Just after the energization, the controller 20 controls all the light emitting means 36 that correspond to the user identification keys 34 such that they are lit or flashed to emit light (S330). This is to prompt the user to depress any of the user identification keys 34.

When, for example, the color of light emitting means A'36a corresponding to the user identification key A34a and the color of light emitting means B'36b corresponding to the user identification keys B34b have different colors such as green and red, the user can memorize his or her user identification key 34 by not only the position and the symbol thereof but also by the color, whereby the user does not forget which user identification key 34 is to be manipulated. Further, when spaces are formed in the peripheries of the user identification keys 34 to adhere seals or write characters therein, the user can immediately recognize which user identification key 34 is to be depressed at the sight of a seal or a character as a mark.

When the user depresses the user identification key A34a, a depression signal is input to the controller 20, whereby the controller 20 detects that the user identification key A34a is depressed (S340). The controller 20 is in a waiting state until it is detected that any of the user identification keys 34 is depressed.

In the example, since the user identification keys 34 are also used as a blood pressure value measurement start key, the controller 20 instructs to start measurement of a blood pressure value in association with the detection of depression of the user identification key A34a (S350). The controller 20 controls a pressurizing pump 16, a slow discharge valve 18b, and a quick discharge valve 18a, whereby the cuff 12 is pressurized and exhausted. Further, the controller 20 stores a detected value of a pressure sensor 12a in a memory 24 through an AD converter in the pressure reducing process of the cuff 12, supplies the stored result to a blood pressure measuring means 26 to cause it to calculate a blood pressure value.

The controller 20 instructs the light emitting means A'36a corresponding to the user identification key A34a depressed previously to emit light during the period of time from the start of measurement of the blood pressure value executed by pressing the cuff 12 to the completion of calculation of the blood pressure value executed after the air in the cuff 12 is exhausted, whereby the user identification key A34a is flashed and the user identification keys B34b is lit off (S360). With this operation, the user can visually recognize that he or she manipulates the user identification key A34a while the blood pressure value is being measured and that the blood pressure value is being measured at present.

When the blood pressure measuring means 26 completes calculation of the blood pressure value (S370), the controller 20 discharges the air in the cuff 12 and displays the blood pressure value as the result of measurement on a display unit 28 as well as stores the blood pressure value in the memory region of the memory 24 corresponding to the user identification key A34a (S380).

Further, when the measured value is displayed on the display unit 28, the controller 20 instructs the light emitting means A'36a corresponding to the user identification key A34a to emit light so that the user identification key A34a is lit (S390). The user can visually recognize that measurement of the blood pressure value is completed and further that the measured value is stored in the memory region corresponding to the user identification key A34a from that the user identification key A34a changes from flash to light.

When any key is not manipulated after a predetermined time (for example, 1 minute) elapses, the power supplied to the sphygmomanometer main body 14 is automatically shut off. The power may be manually shut off by depressing the power supply key 32. Further, after the measured value is displayed on the display unit 28 for a predetermined time, the controller 20 may return to S330 of the flow again and be placed in a state for waiting for the user identification keys 34 to be depressed.

With the above arrangement, since the user cannot start to measure a blood pressure value until he or she depresses at least any of the user identification keys 34, the user does not forget to execute a switching job for switching a user changeover switch, whereby he or she can securely store a measured value to his or her memory region. Moreover, in the example, since the user identification keys 34 are also used as the measurement start key, measurement of a blood pressure value can be started immediately after the user identification keys 34 are manipulated.

Further, the manipulated user identification key 34 is flashed while a blood pressure value is being measured and is lit after completion of the measurement, the user can visually recognize easily which key is manipulated by him or her and further can grasp the process of measurement of a blood pressure value.

EXAMPLE 2

Figure 4:
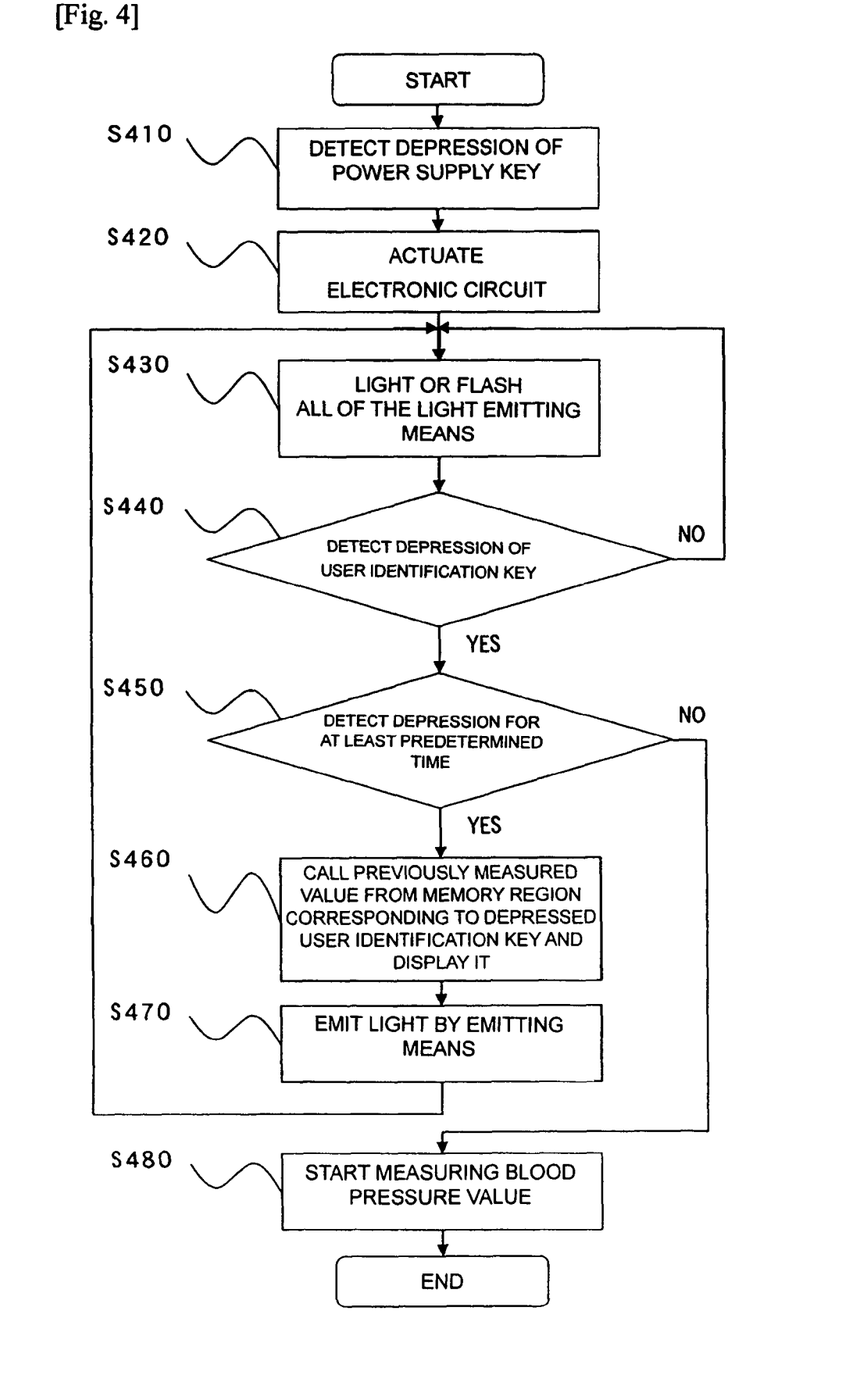
FIG. 4 is a flowchart showing a second example of the electronic sphygmomanometer according to the present invention.

Next, a second example of the electronic sphygmomanometer 10 according to the present invention will be explained with reference to FIG. 4. Since the arrangement of the electronic sphygmomanometer 10 of the example is the same as that explained in the first example, the explanation thereof is omitted. Note that it is assumed also in the example that a user determines that a user identification key A34a is his or her user identification key 34 also in the example.

Since the flow from the detection of depression of a power supply key 32 (S410) to the instruction of light emission to all the light emitting means 36 (S430) is the same as the flow from S310 to S330 of the example 1, the explanation of the flow is omitted.

A controller 20 waits for depression of any of user identification keys 34 to be detected (S440). In the example, after it is detected that the user identification key A34a is depressed by the user, the controller 20 counts a depression time by a timer, and when it is depressed for at least a predetermined time (S450), the controller 20 displays a previously measured value stored in a memory 24 in place of starting measurement of a blood pressure value as in the example 1. Note that it does not matter whether a means corresponding to the timer is realized by an electronic part such as a logic IC and the like or realized by a combination of electric parts including a charge part such as a capacitor and the like.

Specifically, the controller 20 recognizes the user identification key A34a depressed for at least the predetermined time, calls the measured value stored in the memory region of the memory 24 corresponding to the user identification key A34a or the finally stored measured value when a plurality of measured values are stored therein, and displays it on a display unit 28 as the previously measured value of the user (S460).

When the previously measured value is displayed on the display unit 28, the controller 20 instructs the light emitting means A'36a corresponding to the depressed user identification key A34a to flash or light the user identification key A34a by emitting light and lights off the other user identification key B34b (S470). With this operation, the user can visually recognize that he or she displays his or her previously measured value by manipulating the user identification key A34a.

Note that although the user identification key A34a is depressed, when it is not depressed for at least the predetermined time, the controller 20 determines that a blood pressure value is to be measured and starts measuring the blood pressure value (S480).

With the above operation, the user can securely display his or her previously measured value without displaying the previously measured value of any other person in association with manipulation of his or her user identification key 34 and can confirm that his or her previously measured value is displayed.

EXAMPLE 3

Figure 5:
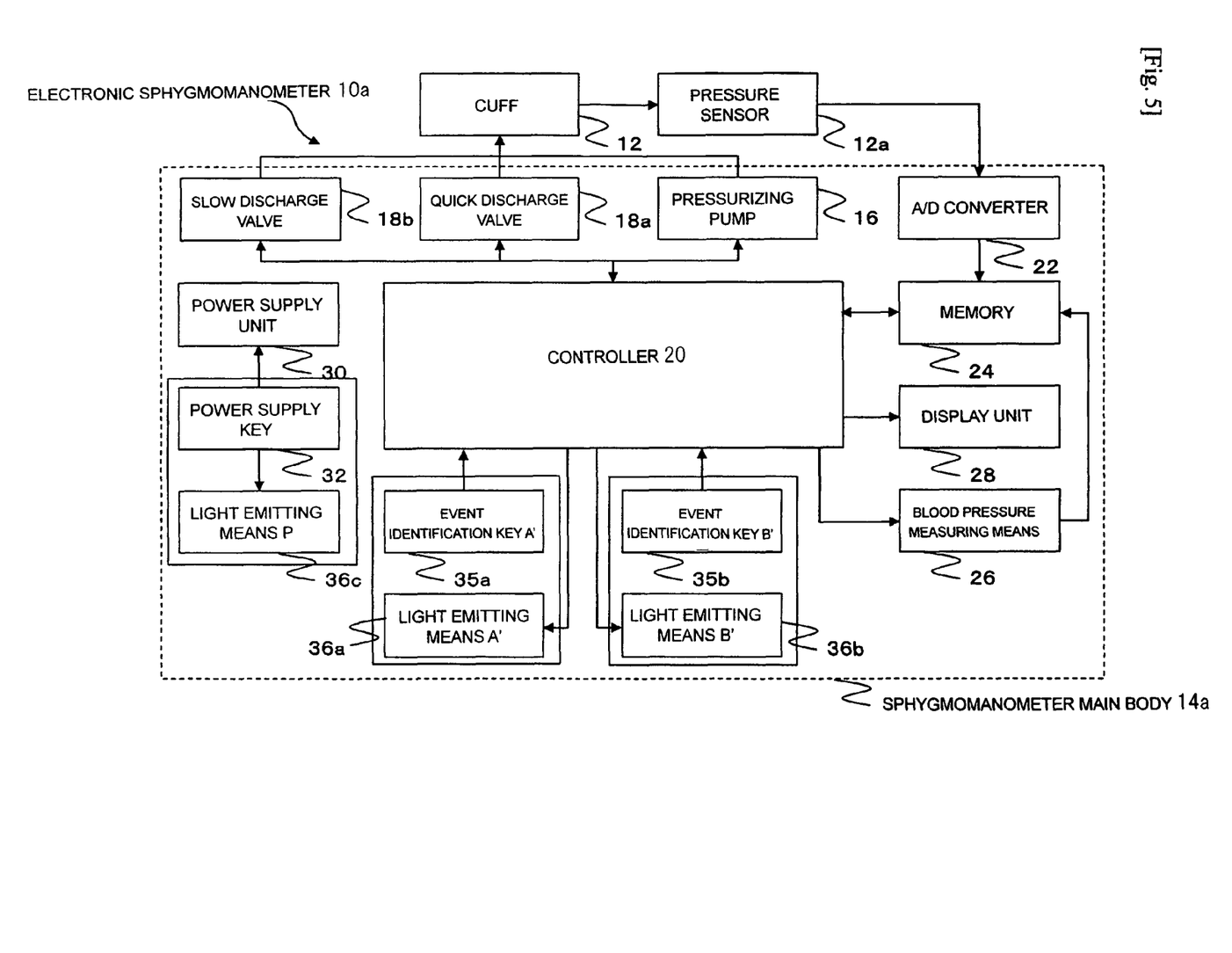
FIG. 5 is a configurational view showing another example of the electronic sphygmomanometer according to the present invention.

Next, a third example of the electronic sphygmomanometer 10 of the present invention will be explained with reference to the configurational view of FIG. 5. In the arrangement of an electronic sphygmomanometer 10a of the example, since the constitutional means, which are the same as those of the electronic sphygmomanometer 10 described above, and the detailed function, the example, and the operation/working-effect of the constitutional means are the same as those described above, the description thereof is omitted.

It is preferable that one set of the electronic sphygmomanometer 10a of the example is fundamentally used by each user. The electronic sphygmomanometer 10a includes a plurality of event identification keys 35, which can be selected in each event, in place of the user identification keys 34 described above, and light emitting means 36 each disposed for each of the event identification keys 35. Note that, in FIG. 5, although the event identification keys 35 include two event identification keys 35a and 35b, the number of the event identification keys 35 need not to be the 2 keys as long as they include a plurality of keys. Further, the shape of the event identification keys 35 and whether or not they have a lock are the same as the user identification keys 34.

The event identification keys 35 are keys for identifying the times at which a blood pressure value is measured such as early morning, before going to bed, and the like and the states of the user when a blood pressure value is measured such as before dosing, after dosing, sitting position, recumbent position, standing position, and the like (hereinafter, they are generically called events), and the keys are provided for each of the events.

Memory regions each secured for each of the event identification keys 35 are formed as many as the event identification keys 35 in a memory 24, and a controller 20 detects the manipulation of the event identification key 35 selected by the user in correspondence to each event and stores a measured blood pressure value in the memory region corresponding to the manipulated event identification key 35. That is, a blood pressure value of each event is stored in the memory 24.

The controller 20 controls the light emission of the light emitting means 36 corresponding to the manipulated user identification key 35 from the start to the end of measurement of a blood pressure value and/or while the blood pressure value is being displayed, whereby, even while a blood pressure value is being measured and displayed, the user can visually confirm securely that the blood pressure value is being measured and displayed, a process of measurement, and the like by selecting an arbitrary event.

Further, a blood pressure measuring means 26 may start measuring a blood pressure value in association with the manipulation of the event identification key 35. According to this operation, since the user does not forget to switch a changeover switch as in a switching job of the changeover switch and further a measured value is securely stored in the memory prepared to each event.

Further, a display unit 28 may display the value previously stored in the memory region of the memory 24 corresponding to the manipulated user identification key 35, that is, the blood pressure value measured last time in the same condition (time, event) in association with the manipulation of the user identification key 35.

Since the blood pressure value measured last time in the same condition is displayed by manipulating the event identification key 35 as described above, it is properly compared with a newly measured blood pressure value.

Since the blood pressure value measured in the same condition is securely stored in the memory region corresponding to the manipulated event identification key 35, it is easy to compare a plurality of blood pressure values with each other in the same condition, to observe the change of a blood pressure value according to an event, and to execute health management using blood pressure value data of each event.

Further, since the electronic sphygmomanometer 10a has a power supply unit 30 similar to that described above, the power supply unit 30 may supply power to a sphygmomanometer main body 14a of the electronic sphygmomanometer 10a in association with the manipulation of the event identification key 35. According to the operation, it is possible to start measuring a blood pressure value and to display it at once without manipulating a power supply key 32.

Further, each of the light emitting means 36 may emit light in a different color for each of the event identification key 35 corresponding to it. According to the arrangement, the user can visually recognize that he or she manipulates the key corresponding to an event and that a blood pressure value in the event is being displayed also by color, in addition to the location where the event identification keys 35 are disposed, and symbols.

It is assumed here that the electronic sphygmomanometer 10a includes, for example, three event identification keys 35, and that the events are previously classified to "morning", "daytime", and "night" which sequentially correspond to event identification keys 35a, 35b, 35c.

When the user measures a blood pressure value in the time zone of "morning", he or she starts measuring the blood pressure value by manipulating the event identification key 35*a*. At the time, the blood pressure value is naturally recorded in the memory region of the memory 24 corresponding to the event identification key 35*a*, supplemental information such as a detailed time (including date) and the like may be further stored in the memory region in association with the blood pressure value. Note that, in this case, the electronic sphygmomanometer 10*a* must include a time measuring means (not shown).

As described above, the supplemental information stored in the memory 24 is helpful to observe, diagnose, and analyze the state of health of the user.

In the electronic sphygmomanometer 10*a* provided with the time measuring means, when the power supply key 32 is manipulated, the controller 20 determines whether the time at which measurement is executed is "morning", "daytime", or "night" based on the present time clocked by the time measuring means and causes the light emitting means 36, which corresponds to the event identification key 35 corresponding to the present time, to emit or flash light. As a result, the user can grasp at a glance which event identification key 35 is to be manipulated to measure a blood pressure value at the time.

Although the examples of the electronic sphygmomanometer are described above, the electronic sphygmomanometer of the present invention is by no means limited to those provided with all the constituents described in the examples and may be variously modified and corrected. Further, it is needless to say that these modifications and corrections are within the scope of claims of the present invention.

For example, the electronic sphygmomanometer may be provided with both the two types of the user identification keys 34 and the event identification keys 35, and the shapes and the disposing positions of the keys and the colors of the light emitting means 36 may be changed according to the types of the identification keys. Further, when both the two types of the keys are provided, a measured value may be stored in the respective regions of the memory 24 corresponding to the respective keys by manipulating the two types of the keys.

REFERENCE NUMERALS

10: electronic sphygmomanometer
12: cuff
12*a*: pressure sensor
14: sphygmomanometer main body
16: pressurizing pump
18*a*: quick discharge valve
18*b*: slow discharge valve
20: controller
22: A/D converter
24: memory
26: blood pressure measuring means
28: display unit
30: power supply unit
32: power supply key
34: user identification key
34*a*: user identification key A
34*b*: user identification key B
35: event identification key
36: light emitting means
36*a*: light emitting means A'
36*b*: light emitting means B'
36*c*: light emitting means P

The invention claimed is:

1. An electronic sphygmomanometer comprising:
a blood pressure measuring device that outputs a blood pressure value;
a display unit for displaying the blood pressure value;
user identification keys, each of said user identification keys corresponding to selectable manipulation thereof by a respective one of different users;
a memory having memory regions, a particular one of said memory regions being uniquely associated with a corresponding one of said user identification keys, the particular one of the memory regions being addressed in response to manipulation of a corresponding one of said user identification keys to allow storage of respective data for each of said different users in a different one of the memory regions by manipulation of the corresponding one of said user identification keys by the respective one of the different users to which the corresponding one of the user identification keys is allocated; and
light emitters each being disposed at, or proximate to, a respective one of said user identification keys, a one of the light emitters, associated with the corresponding one of the user identification keys being manipulated, emitting light while the blood pressure is being measured or displayed.

2. The electronic sphygmomanometer according to claim 1, wherein the blood pressure measuring device starts measuring a blood pressure value in association with the manipulation of a one of the user identification keys.

3. The electronic sphygmomanometer according to either of claim 2 or 1, wherein the display unit displays a previously stored value stored in a one of the memory regions of the memory corresponding to a manipulated one of said user identification keys associated therewith.

4. The electronic sphygmomanometer according to either of claim 2 or 1, further comprising:
a power supply unit for supplying operation power to electric/electronic circuits in a main body,
wherein the power supply unit supplies the power to the inside of a main body in association with the manipulation of said one of said user identification keys.

5. An electronic sphygmomanometer according to either of claim 2 or 1,
wherein the light emitters emit light of different color for each of the user identification keys corresponding to the light emitters.

6. An electronic sphygmomanometer comprising:
a blood pressure measuring device that outputs a blood pressure value;
a display unit for displaying the blood pressure value;
event identification keys;

a memory having memory regions for storing different events, a particular one of said memory regions being uniquely associated with a corresponding one of said event identification keys, the particular one of the memory regions being addressed in response to manipulation of a corresponding one of said event identification keys to allow storage of respective data for each of said different events in a different one of the memory regions by manipulation of the corresponding one of said event identification keys; and light emitters each being disposed at or proximate to a respective one of said event identification keys, a one of the light emitters, associated with the corresponding one of the event identification keys being manipulated, emitting light while the blood pressure is being measured or displayed.

7. An electronic sphygmomanometer according to claim 6, wherein the blood pressure measuring device starts measuring a blood pressure value in association with the manipulation of a one of the event identification keys.

8. The electronic sphygmomanometer according to either of claims 7 or 6, wherein the display unit displays a previously stored value stored in a one of the memory regions of the memory corresponding to a manipulated one of said event identification keys.

9. The electronic sphygmomanometer according to either of claim 7 or 6, further comprising:

a power supply unit for supplying operation power to electric/electronic circuits in a main body, wherein the power supply unit supplies the power to the inside of the main body in association with the manipulation of a selected one of the event identification keys.

10. The electronic sphygmomanometer according to either of claim 7 or 6, wherein the light emitters emit light of different color for each of the event identification keys corresponding to the light emitters.

11. The electronic sphygmomanometer according to claim 7 or 6, wherein the memory stores at least one item of supplemental information in association with the blood pressure value.

12. The electronic sphygmomanometer according to either of claim 7 or 6, further comprising:

a time measuring device, wherein, a one of the light emitters corresponding to an associated one of said event identification keys that corresponds to a present clock time determined by the time measuring device, emits light.

\* \* \* \* \*